United States Patent [19]

Siiman et al.

[11] Patent Number: 5,169,754

[45] Date of Patent: Dec. 8, 1992

[54] BIODEGRADABLE PARTICLE COATINGS HAVING A PROTEIN COVALENTLY IMMOBILIZED BY MEANS OF A CROSSLINKING AGENT AND PROCESSES FOR MAKING SAME

[75] Inventors: Olavi Siiman, Davie; Alexander Burshteyn, Miami Lakes; Ravinder K. Gupta, Pembroke Pines, all of Fla.

[73] Assignee: Coulter Corporation, Hialeah, Fla.

[21] Appl. No.: 607,253

[22] Filed: Oct. 31, 1990

[51] Int. Cl.⁵ .................... C12Q 1/00; G01N 33/544
[52] U.S. Cl. ........................................ 435/5; 436/524; 436/526; 436/531; 436/532; 428/403; 428/407; 427/131; 427/213.35; 427/216
[58] Field of Search ............... 435/5; 436/524, 526, 436/531, 532; 428/403, 407; 524/22; 427/127-132, 213.35, 216, 217

[56] References Cited

U.S. PATENT DOCUMENTS

| | | | |
|---|---|---|---|
| 3,970,518 | 7/1976 | Giaever | 435/5 |
| 4,010,038 | 3/1977 | Iwasaki et al. | 424/492 |
| 4,210,418 | 7/1980 | Brown et al. | 422/57 |
| 4,253,844 | 3/1981 | Limet et al. | 435/180 |
| 4,267,234 | 5/1981 | Rembaum | 428/403 |
| 4,358,388 | 11/1982 | Daniel et al. | 252/62.54 |
| 4,452,773 | 6/1984 | Molday | 436/530 |
| 4,454,234 | 6/1984 | Czerlinski | 436/526 |
| 4,478,946 | 10/1984 | Van der Merwe et al. | 436/518 |
| 4,554,088 | 11/1985 | Whitehead et al. | 436/527 |
| 4,582,622 | 4/1986 | Ikeda et al. | 436/526 |
| 4,783,336 | 11/1988 | Margel et al. | 436/532 |
| 4,795,698 | 1/1989 | Owen et al. | 436/526 |
| 4,920,061 | 4/1990 | Poynton et al. | 436/526 |
| 4,965,007 | 10/1990 | Yudelson | 428/403 |

FOREIGN PATENT DOCUMENTS 8303920 11/1983 PCT Int'l Appl. .

OTHER PUBLICATIONS

K. Nustad et al., "Monodisperse Polymer Particles in Immunoassays and Cell Separation", *Microspheres, Medical and Biological Applications*, A. Rembaum and Z. A. Tukes, Eds. (Boca Raton: CRC Press, 1988) Chapter 4 pp. 53-75.

C. D. Platsoucas et al., "The Use of Magnetic Mono-sized Polymer Particles for the Removal of T cells from Human Bone Marrow Suspension", *Microspheres: Med. and Biol. Appl.*, Op. cit., Chapter 6, pp. 89-98.

*Primary Examiner*—Esther L. Kepplinger
*Assistant Examiner*—Christopher L. Chin
*Attorney, Agent, or Firm*—Myron C. Cass

[57] ABSTRACT

The invention relates generally to colloidal particles having a crosslinked coating with pendent functional groups attached thereto. Magnetic and non-magnetic particles have a biodegradable, crosslinked gelatin coating to which is covalently attached pendent biological substances or molecules, especially monoclonal antibodies. The monoclonal antibodies so attached are useful in a variety of positive and negative biological assays.

48 Claims, No Drawings

BIODEGRADABLE PARTICLE COATINGS HAVING A PROTEIN COVALENTLY IMMOBILIZED BY MEANS OF A CROSSLINKING AGENT AND PROCESSES FOR MAKING SAME

RELATED INVENTION

This invention is related to U.S. Pat. No. 5,062,991, filed Jun. 4, 1990 and issued Nov. 5, 1991, and entitled "IN SITU USE OF GELATIN IN THE PREPARATION OF UNIFORM FERRITE PARTICLES". These applications are owned by a common assignee.

FIELD OF THE INVENTION

This invention relates generally to colloidal sized particles having a crosslinked gelatin coating with pendent functional groups attached thereto. Specifically, this invention relates to colloidal particles having a crosslinked gelatin coating that is functionalized to bind a pendent protein such as an antibody, to the method of making such particles and to the use of such particles in biological assays.

BACKGROUND OF THE INVENTION

The use of polymeric particles and magnetic particles to bind a compound has long been known and used in industrial and laboratory procedures. For example, the Merrifield resins, crosslinked styrene-divinylbenzene spheroidal beads, were among the earliest and most widely used modern substrate particles. They were used in organic synthesis, for heterogenizing homogeneous catalysts and in biochemical reactions. Since the Merrifield resins were fairly large, they could easily be separated by filtration. In some fields, however, it is desirable to use colloidal sized particles because the material to be bound is scarce, expensive or is to be used in a procedure where larger particles are not desirable. This is particularly true in the biochemical field. When particles are of colloidal size, however, their separation from liquid medium by filtration can become lengthy and difficult. In particular, colloidal particles tend to coat the surface of the filter and slow the process. The use of magnetic particles, specifically magnetic particles having a polymeric coating, has found great utility because such particles can be magnetically gathered to one side of a reaction vessel and the bulk of the reaction medium simply decanted. (The word "particles" as used herein encompasses spheres, spheroids, beads and other shapes as well. These words are used interchangeably unless otherwise specified.) The use of coated magnetic particles has found a particular utility in biological applications, especially where antibodies are bound to the surface coating of the particles. The bound antibodies may then be used to capture a specific biological substance from a test sample containing numerous biological samples or to capture undesired species from the test sample, leaving the desired species in the sample.

The categories of coated magnetic particles, also known as magnetic spheres or beads, can be divided into four general classes.

1. Core-and-shell beads with a magnetic core and a hard shell coating of polymerized monomer or a silanizing agent. See Rembaum U.S. Pat. No. 4,267,234 (polyglutaraldehyde shell around ferrofluid core particles); Czerlinski U.S. Pat. No. 4,454,234 (suspension or emulsion polymerized coating around submicron magnetic particles); Whitehead et al. U.S. Pat. No. 4,554,088 (silanized magnetic oxide particles of polydisperse size and shape); and Margel et al. U.S. Pat. No. 4,783,336 (suspension polymerized polyacrolein around ferrofluid particles).

2. Core-and-shell beads with a magnetic core and a loose shell of random coil or globular polymer which may or may not be crosslinked. See Molday U.S. Pat. No. 4,452,773 (dextran coating around ferrofluid particles) and Owen et al. U.S. Pat. No. 4,795,698 (protein such as bovine serum albumin around ferrofluid particles.

3. Magnetic latex materials formed by uniformly embedding ferrofluid particles in polystyrene latex particles. See Daniel et al. U.S. Pat. No. 4,358,388.

4. Porous polymer particles filled with magnetic materials such as polymer-ferrite or polymer maghemite composite systems. See K. Nustad et al. "Monodisperse Polymer Particles In Immunoassays And Cell Separation", *Microspheres: Medical and Biological Applications*, A. Rembaum and Z. Tökès, eds. (Boca Raton, Fla.: CRC Press, 1988) pages 53–75; C. D. Platsoucas et al., "The Use Of Magnetic Monosized Polymer Particles For The Removal Of T Cells From Human Bone Marrow Cell Suspensions", ibid. at pages 89–99; and International Patent Publication No. WO 83/03920, Ughelstad et al. (polymer coated magnetic particles prepared by treating compact or porous particles with a solution of iron salts and the use of such particles for medical, diagnostic or other purposes).

The usefulness of most polymer coated magnetic beads in medical and biological applications has been limited by practical considerations such as the uniformity of particle size and shape, the need for the biological reagent to be strongly bound to the particle, a preference for hydrophilic polymer coatings as opposed to hydrophobic coatings, and whether or not the coating is biodegradable. While biodegradability is of particular importance where a biological reagent is to be administered in vivo, it is also important in various cell sorting, separation and assay procedures. The most desirable coated magnetic particles would have the following features.

1. The particles should be as small as possible in order to maximize the surface area on which the biological reagent is coated, but the particles should still be easily separable with a small magnet. Small size and large surface area are desirable in order to use the least possible quantity of particles to remove the targeted substance; e.g., to interact with on the order of $10^6$ cells per sample in one step, thereby avoiding sequential additions and work-ups.

2. There should be a low non-specific binding of the antibody-coated particles to cell surfaces. The particle surface should be hydrophilic or covered with a coating of a hydrophilic substance to which the antibody is attached.

3. The polymer and antibody layers on the particles should be covalently bound to each other in order to reduce dissociation and conformational changes.

4. The coating on the magnetic particles and any molecular chains which link an antibody to the polymer surface should be metabolizable.

5. In positive selection of cells, a mechanism for quickly and easily recovering viable cells from the magnetic particles should be available in order that recovered cells can be cultured.

6. In the negative selection of cells, the antibody-coated particles should be sterile so that the remaining cells can be cultured.

In addition to magnetic particles, there is also a need for polystyrene latex (PSL) particles which have been coated with hydrophilic polymer coatings to which antibodies can be subsequently bound. These polymer coated PSL particles can be used in bead-based cell population analyses and immunoassays. However, non-magnetic PSL particles, as made, usually have a relatively low density of various functional groups such as carboxyl or amino groups. Consequently, covalent coupling of coating materials such as dextran or gelatin to the surface of PSL particles is not satisfactory.

The various particles described above have been used in the biological arts to immobilize a variety of biological substances, particularly antibodies. In using such particles, immobilization of antibodies by covalent coupling is preferred to immobilization by antibody adsorption which requires careful and separate adjustment of pH and antibody concentration for each monoclonal antibody used. P. Bagchi et al., *J. Colloid Interface Sci.*, 83:460–478 (1981); J. Lyklema, *Colloids and Surfaces*, 10:33–42 (1984); M. D. Bale et al., *J. Colloid Interface Sci.*, 125:516–525 (1988); C. C. Ho et al., ibid., 121:564–570 (1988); "Proteins at Interfaces: Physicochemical and Biochemical Studies", *ACS Symposium Series*, No. 343, J. L. Brash and T. A. Horbett, Eds. (Washington: Amer. Chem. Soc., 1987); W. Norde, *Adv. Coll. Interface Sci.*, 25:267–340 (1986); A. V. Elgersma et al., *Abstracts of the 198th Amer. Chem. Soc. Meeting*, Miami Beach, Fla., Sept. 10–15, 1989, COLL 0131; and D. E. Brooks, Annenberg Center for Health Sciences and H. B. Wallis Research Facility at Eisenhower Latex Conference, Orlando, Fla., Dec. 4–5, 1989. However, even when the pH and antibody are carefully controlled, there is little assurance that the orientation of adsorbed antibody will be such that an active adsorbed antibody will result. Adsorbed antibodies also have long term storage problems arising from antibody desorption from the particles' surfaces. Furthermore, proteins, such as antibodies, tend to achieve maximum adsorption on hydrophobic surfaces at or near the pI of the protein. However, if electrostatic interactions between charge groups are important, then the adsorbing surface and the adsorbate should have net opposite charges. Covalent coupling methods, on the other hand, are not as sensitive to these conditions.

Covalent coupling methods have been used with particles of magnetite embedded in carboxy-modified latex subsequently coated with aminodextran and derivitized with a number of antibodies. R. S. Molday et al. *FEBS. Lett.*, 170:232–238 (1984). If the antibody is of IgG isotype, the covalent coupling method assures that the linkage between the antibody and the particles occurs at the antibody's Fc or hinge region, and not at the antibody's Fab region. If the antibody is of pentameric IgM isotype which has only Fab regions exposed, the coupling of one Fab region to the particle will still leave four Fab regions exposed and available for reaction.

This invention provides for the preparation of magnetic and non-magnetic particles having a biodegradable coating to which can be attached pendent biological substances, such as monoclonal antibodies. The particles of the invention can be used in various cell separation and assay methodologies. Biodegradability in the coating used on the magnetic or latex core material is important in cell separation technology. For example, antibodies may be conjugated to gelatin coated magnetic particles such as manganese ferrite particles. These particles would thus contain a proteinaceous coating and a manganese-iron oxide core, all of which are biodegradable. In a positive cell selection procedure using such particles, once the desired cell has been isolated from other cells, the particles and coating can be allowed to degrade in a manner such that the cells are kept viable and can be cultured for further use. Alternatively, the enzyme collagenase can be used first to release the core material (magnetic or latex) by digestion of the gelatin coating. The core material can then be removed from the cell suspension before culturing the cells. In the negative selection of cells with such biodegradable beads, the beads can be left in the cell suspension from which targeted cells were removed without compromising the viability of the remaining cells. For example, in bone marrow purging operations using biodegradable magnetic beads, there is less concern about leaving behind some beads in the purged marrow that is to be transplanted in a patient. Currently, synthetic polymer-magnetite particles prepared by Ugheltad et al, International Patent Publication No. WO 83/03920, and conjugated with antibody are being used in bone marrow purging. The polymer is not biodegradable and imparts a hydrophobic surface to these beads. This hydrophobicity, which is not present in the gelatin coated particles of the claimed invention, is responsible for non-specific interactions between the beads and cells. As a result of this non-specific interaction, the selectivity is poor and more beads must be used to attain the desired level of treatment. The claimed invention avoids these problems.

SUMMARY OF THE INVENTION

The invention provides a method for the preparation of discrete colloidal particles having a solid core and coated with a water soluble gelatin or derivative thereof, said coating being crosslinked or fixed by the action of a chemical crosslinking agent and having a plurality of pendent functional groups. The pendent functional groups may be or have terminal aldehyde or carboxylate groups, amine groups, sulfhydryl groups or maleimidyl groups, and polyclonal or monoclonal antibodies.

The invention provides discrete colloidal particles having pendent biological functional groups such as polyclonal and monoclonal antibodies covalently attached to the crosslinked gelatin coating by means of a derivatized short diamine or polyamine chain so as to enable advantageous use of said antibody functionalized particles in biological separations and assays. The derivatized diamine or polyamine chain acts as a bridging group between the biological substance or functional group and the crosslinked gelatin.

The invention provides a process for the preparation of discrete colloidal particles having a solid core coated with a biodegradable, crosslinked gelatin or gelatin derivative having pendent functional groups. The process comprises coating a solid core material which has a hydrophobic surface with gelatin or a gelatin derivative, crosslinking the adsorbed gelatin and derivatizing the crosslinked gelatin to obtain a product having a desired reactive species covalently bound to said crosslinked gelatin surface. The invention further provides a process for the preparation of particle bound polyclonal and monoclonal antibodies.

The invention provides a process for the separation, either positive or negative, and analysis of biological substances comprising contacting a solution containing a biological substance with an antibody covalently bound to the surface of a crosslinked gelatin coated solid core particle, incubating the resultant mixture at a temperature and for a time sufficient to form a complex between said antibody and said substance, separating the particles from the solution and analyzing the particles or the solution for the presence and/or absence of the desired substance.

DETAILED DESCRIPTION OF THE INVENTION

In the Detailed Description Of The Invention and Preferred Embodiments which follow, applicants place reactive maleimidyl groups on the crosslinked gelatin coated particles and reactive sulfhydryl groups on the antibodies. These may be reversed such that the maleimidyl groups are attached to the antibodies and the sulfhydryl groups are attached to the crosslinked gelatin. Applicants have also elected to use 2-iminothiolane hydrochloride as the model for the sulfhydryl reagent and sulfo-SMCC (described below) as the model for the maleimidyl reagent. Other reagents enumerated or of like nature and result may also be used.

Glossary of Biological Reagents

All of the monoclonal antibodies (Ab) referred to herein are identifying designations used by Coulter Corporation, Hialeah, Florida for monoclonal antibodies made by Coulter Corporation. The following information further identifies the antibodies used herein. The use of these monoclonal antibodies is by way of example only and is not to be understood as limiting the invention. The term "CD" refers to "Cluster Designation" adopted by the International Workshops on Human Leukocyte Differentiation Antigens. A.T.C.C. is the American Type Culture Collection, Rockville, Maryland.

| Antibody | CD | Description or Reference |
|---|---|---|
| T11 | CD2 | Derived from hybridization of mouse NS/1-AG4 cells with spleen cells of BALB/cJ mice immunized with T cell chronic lymphocytic leukemia cells. |
| T4 | CD4 | As T11, but immunized with peripheral human T lymphocytes. |
| T8 | CD8 | As T11, but immunized with human thymocytes. |
| KC16 | — | U.S. Pat. No. 4,752,563; A.T.C.C. Deposit No. CRL 8994. |
| 1D3 | — | U.S. Pat. No. 4,931,395; A.T.C.C. Deposit No. HB 9445 |
| KC48 | — | U.S. Pat. No. 4,865,971; A.T.C.C. Deposit No. HB 9584 |
| MO2 | CD14 | R. F. Todd et al, J. Immunol., 126:1435 (1981). |
| PLT-1 | — | R. F. Todd et al., Blood, 59:775 (1982); Griffith et al., Blood, 61:85 (1983). |

Other reagents used herein and commercially obtainable from Coulter Corporation are:

| | |
|---|---|
| MsIgG1-RD1/MsIgG1-FITC: | Mouse IgG1-phycoerythrin [RD1]/Mouse IgG1-Fluorescein Isothiocyanate [FITC]. |
| T11-RD1/B4-FITC: | Ab T11-phycoerythrin/Ab B4-FITC. |
| T4-RD1/T8-FITC: | Ab T4-phycoerythrin/Ab T8-FITC. |

Detailed Description

In using the method of the invention, uniform particles (the core material) in the size range of 0.1 to 5.0 microns are coated with gelatin or a gelatin derivative, and the coating is fixed by means of a chemical fixing agent. The uncoated particles have a hydrophobic or partially hydrophobic surface. The preferred size of the particles is in the range of 0.1 to 1.0 microns.

The magnetic particles used in the claimed invention may be preformed magnetic particles that are dispersible in a gelatin solution or they may be magnetic particles prepared by the in situ use of gelatin in the preparation of said magnetic particles. The in situ method for the preparation of monodispersed colloidal particles of ferrites of manganese, zinc, mixed manganese-zinc, iron, barium, cobalt and nickel involves the use of an aqueous metal hydroxide gel first formed by mixing ferrous and other metal salts in an aqueous gelatin solution with potassium or sodium hydroxide and potassium or sodium nitrate solution, all solutions being purged with nitrogen gas. The conversion of the gel to the metal oxide sol is achieved by mild thermal treatment at 90° C. (low temperature) for 4-72 hours, during which nitrate oxidation of ferrous iron occurs. The magnetic particles in the hydrosol are then washed and resuspended in a 1% aqueous solution of gelatin of the type described below prior to further treatment as described herein. In preparing magnetic particles using in situ gelatin as described herein, only one type of gelatin has been found optimal for such use. This is type B or alkali-cured gelatin with a pI range of 4.75 to 5.0. The procedures for the preparation of magnetic particles using in situ gelatin are fully described in U.S. Pat. No. 5,062,991, the teachings of which is incorporated here by reference, and also described herein. The gelatins which are crosslinked according to the present invention are given below.

Gelatin is obtained from highly crosslinked collagen in fibrous tissue, such as skin or bone, which has been acid or base cured and then thermally degraded at or above 39° C. The collagen molecule combines the helical structure of the α-type proteins with the inter-chain hydrogen bonding of the β-type proteins. The three collagen peptide chains, each in the form of a left handed helix, are twisted about each other to form a superhelix. Upon treatment, the three peptide strands of the superhelix are separated by the breaking of inter-chain hydrogen bonds and replacing them with hydrogen bonds to water molecules. The separated peptides have random coil configurations. "The Theory of the Photographic Process", T. H. James, Ed., (New York: MacMillan Press, 1977). The α-1 peptide chain has been sequenced and found to have over 1000 residues. D. J. S. Hulmes et al., *J. Mol. Biol.*, 79:137 (1973). They contain extensive segments of mainly non-polar residues; and the polar residues which are present are not localized into acidic or basic regions. Furthermore, in contrast to globular proteins which tend to expose their hydrophilic residues on their surfaces and bury their hydrophobic residues within their structure {see R. E. Dickerson et al., "The Structure and Action of Proteins", (Menlo Park: Benjamin, 1969)}, random coil gelatin has exposed hydrophobic residues readily available for adsorption onto the surface of hydrophobic particles such as polystyrene latex particles or magnetite and ferrite particles. When aqueous gelatin is adsorbed onto the surface of a particle, its hydrophilic side chains (aspartyl, glutamyl and lysyl residues) tend to be directed externally to the aqueous medium. The lysyl groups, which function as the intramolecular crosslinkage points in collagen, will be accessible for cross linking in the adsorbed gelatin. Glutaraldehyde is frequently used as the crosslinking agent. Van Der Merwe et al. U.S. Pat. No. 4,478,946 and S. B. Sato et al., J. Biochem., 100:1481-1492 (1986).

A number of different, usually bifunctional, crosslinking agents such as bis [2-(succinimidooxycarbonyloxy)-ethyl]sulfone, disuccinimidyl tartarate, ethylene glycol bis (succinimidylsuccinate), disuccinimidyl suberate and glutaraldehyde may be used in the claimed invention. Glutaraldehyde, the preferred gelatin crosslinking agent, as commercially available, contains mainly monomer absorbing at 280 nm (nanometers). However, there is present in the commercial product a significant amount of polymeric material which gives rise to an absorbance at 235 nm. The polymeric species, probably trimers or linear oligomers, are of sufficient length to form intra- and inter-molecular bridges between amino groups present on the adsorbed gelatin. By judiciously selecting the reaction time between the adsorbed gelatin and glutaraldehyde, the gelatin can be suitably fixed on the core particles so that it will not be removed during subsequent separation, reaction and washing steps. Large flocs created by excessive crosslinking of free gelatin can thereby be avoided and interparticle crosslinking is negated.

Several types of gelatin are available for use in the present invention, such as type A, acid cured, isoelectric point pH 8.3-8.5 and type B, alkali cured, isoelectric point, pH 4.75-5.0. Each type is available in a variety of Bloom Numbers which indicate gel strength. Type A gelatin Bloom Numbers useful in the claimed invention range from 60 to 300. Type B Bloom Numbers useful in the claimed invention range from 60 to 225. The type A, 175 Bloom gelatin used in the preferred embodiment of the claimed invention is preferred and was selected for its relatively large number of lysyl residues and its lower Bloom number in order to minimize intermolecular interactions between gelatin molecules. For optimum adsorption on magnetite and ferrite particles, it was buffered to pH 8.4, the middle of its isoelectric point range, at which pH it is most soluble in water and gives the least viscous solution. The instability of gelatin adsorbed on ferrite particles, which instability arises when glutaraldehyde is added, was overcome by the present invention by the use of more dilute particle and gelatin concentrations [0.1% weight/volume (w/v) instead of the 2.5% w/v solids suspension that was used in other reactions herein] in conjunction with an inert polymeric stabilizer, polyvinylpyrrolidone (PVP), that does not react with glutaraldehyde. The use of the stabilizer and the 25-fold lower gelatin concentrations avoids interparticle crosslinking during the glutaraldehyde fixation reaction. Since polymer desorption is a very slow process relative to the time of the glutaraldehyde fixation reaction, approximately 6 minutes, a stable gelatin coating around the core particle was produced.

In order to be useful in the biological and medical arts, the fixed (crosslinked) gelatin coating should contain functional groups which can be conjugated with biologically active substances such as antibodies to produce immobilized biologically active substances attached to the particle surface. Covalent coupling of biological substances to the particle surface is preferred over simple adsorption. The coupling of an antibody, either polyclonal or monoclonal, to the crosslinked gelatin surface is accomplished by the use of "short chain" diamines or polyamines and a heterobifunctional reagent. (Hereafter, the word polyamine includes diamines). The polyamine is reacted with residual aldehyde or carboxyate groups, either naturally occurring or present by the steps of this invention, present on the crosslinked gelatin surface. The use of polyamine serves not only to block aldehyde/carboxylate groups, but also serves to replenish gelatin amino groups such as lysyl amino groups which were depleted during the crosslinking process. This procedure is generally accomplished in two steps. In the first step, unreacted terminal aldehyde groups are reacted with a polyamine followed by sodium borohydride ($NaBH_4$) reduction of the resulting Schiff's base to create stable, saturated C-N linkages. In the second step, exposed carboxylic acid residues (glutamic, aspartic) of gelatin are coupled to polyamine in the presence of a water soluble carbodiimide such as 1-ethyl-3-(3-dimethylaminopropyl)-carbodiimide (EDAC).

Short chain diamines or polyamines are preferred in order to avoid crosslinking neighboring aldehyde or carboxylic acid groups on the same particle or to avoid linking such groups on different particles. One polyamine amine group reacts with the gelatin surface and the other(s) remains unreacted and available for coupling, directly or indirectly, to a biological substance. Examples of 'short chain' diamines or polyamines include ethylenediamine, phenylenediamine, propylenediamine, 1,4-cyclohexanediamine, cyclohexenediamine, tetramethylenediamine, diethylenetriamine, 1,5-diamino-3-(2-aminoethyl)pentane [$(H_2NCH_2CH_2)_3C$] and the like. Ethylenediamine is preferred.

The coupling of the biological substance to the particle involves activation of the free amino groups of the gelatin-coated particles with a water soluble heterobifunctional reagent such as 2-iminothiolane hydrochloride (IT), sulfosuccinimidyl-4-(N-maleimidomethyl)cyclohexane-1-carboxylate (sulfo-SMCC), m-maleimidobenzoyl-N-hydroxysuccinimide ester, N-succinimidyl-3-(2-pyridyldithio)propionate, succinimidyl-4-(p-maleimidophenyl)butyrate, N-succinimidyl-(4-iodoacetyl)aminobenzoate, the reagents listed above as substitutes for glutaraldehyde and the like. The 2-iminothiolane hydrochloride and the maleimidyl/succinimidyl reagents are preferred. E. Ishikawa, Immunoassay Supp., 1:1-16 (1980) and J. Immunoassay, 4:209-227 (1983); M. Imagawa et al., J. Appl. Biochem., 4:41-57 (1982); and M. D. Partis, J. Protein Chem., 2:263-277 (1983). When using sulfo-SMCC, the active sulfosuccinimidyl ester end of sulfo-SMCC will react at pH 7.0-7.5 with amines to give peptide bonds. The sulfo-SMCC/diamine bridging unit which results is approximately 16 Angstroms in length.

When performing the polyamine and sulfo-SMCC reactions, particle aggregation was monitored by microscopic examination (1000× magnification) and by light scattering analysis using a Coulter $N_4MD$ submicron particle size analyzer (COULTER CORPORATION, Hialeah, Florida), or similar instrument.

The maleimidyl group of sulfo-SMCC will react at pH 6.5-7.5 with free sulfhydryl groups to form a stable, covalent thioether bond. However, it is essential that the coated particles with which sulfo-SMCC is reacted contain no free sulfhydryl groups which could react with the maleimidyl end of sulfo-SMCC. Sulfhydryl groups are found on or generated from cystine and cysteine amino acid residues of which gelatin has very few. Consequently, the crosslinked gelatin particles of the claimed invention do not require a protein modifier to block free sulfhydryl groups prior to reaction with sulfo-SMCC.

Biological substances, particularly either monoclonal or polyclonal antibodies, can be covalently linked to the maleimidyl end of sulfo-SMCC functionalized particles by means of sulfhydryl groups present, either naturally or by derivatization, on said biological substances. Biological substances which have cysteinyl residues inherently contain sulfhydryl groups. To introduce additional sulfhydryl groups, the biological substances' amine groups are activated with Traut's reagent, 2-iminothiolane hydrochloride (IT), at a pH in the range of 7-10. M. Erecinska, *Biochem. Biophys. Res. Commun.*, 76:495-500 (1977); J. M. Lambert et al., *Biochemistry*, 17:5406-5416 (1978); and M. E. Birnbaumer et al., *Biochem J.*, 181:201-213 (1979). When the bio-substances are antibodies, antibody lysyl and terminal amine groups are activated by IT. In the present invention, reaction conditions and the concentration of reactants were varied to determine the optimal coupling so that the bio-substance, especially antibody, when conjugated with the substrate particles, retains its maximum functional activity. Although maleimides react quite rapidly with sulfhydryl groups in solution, the same groups immobilized on particles were given longer reaction periods to react with protein. Particle and antibody concentrations during antibody conjugation were optimized to avoid aggregation, particularly when IgM antibodies were used. The procedures optimized for IgM antibodies can be used for all monoclonal antibodies with an isoelectric point range of about 5.0 to about 9.0. Generally, about 30-fold less antibody was required to achieve covalent coupling than is required for simple adsorption; a consequence of importance where expensive or hard to obtain antibodies are involved.

The optimum concentration of iminothiolane-activated antibody to use in conjugation reactions with maleimidyl-activated particles was determined by the use of activated antibody binding curves (Total Antibody vs Surface Antibody Concentration). After a typical conjugation period, a sample is taken and filtered through a 0.2 μm low-protein binding filter. The filtrate is analyzed spectrophotometrically. The surface antibody is determined by the difference between the total antibody in the starting solution and the antibody in the filtrate (Total Antibody—Filtrate Antibody). The binding data in antibody (Ab) concentration dependent runs show Langmuir isotherm-type characteristics; i.e., a linear low concentration region for total antibody versus surface antibody concentration, a smooth inflection point and a plateau indicating saturation at the particle surface at high concentrations. The antibody concentrations actually used were those at the inflection point or at concentrations slightly above the infection point. Binding constants were obtained graphically by recasting the equation of a hyperbola into one for a straight line. A double reciprocal plot of $1/n_2^2$ versus $1/C_2$ was constructed, where $n_2^s$ is the number of moles of IT-Ab bound per gram of particles and $C_2$ is the molar concentration of free IT-Ab at equilibrium. Linear plots are indicative of Langmuir-type binding behavior. The binding constants $K_1 = n^sK$ of IT-Ab for sulfo-SMCC-activated ferrite particles were calculated using the equation $1/n_2 = 1/(n^sKC_2) + 1/n^s$, where K is the intrinsic binding constant and ns is the number of moles of binding sites per gram of ferrite particles. Linear regression analysis of plots for various monoclonal antibodies gave the following results:

| Ab T11:  | $K = 1.3 \times 10^6 M^{-1}$ | $n^s = 5.9 \times 10^{-8}$ mol/g |
|---|---|---|
| Ab KC16: | $K = 6.4 \times 10^6 M^{-1}$ | $n^s = 5.1 \times 10^{-7}$ mol/g |
| Ab 1D3:  | $K = 2.7 \times 10^6 M^{-1}$ | $n^s = 2.0 \times 10^{-7}$ mol/g |
| Ab MO2:  | $K = 1.8 \times 10^7 M^{-1}$ | $n^s = 7.1 \times 10^{-7}$ mol/g |

The results for the ferrite particles compare favorably with similar data for commercially available carboxy-modified latex beads (23% magnetite, 0.980 μm dia., obtained from Rhone-Poulenc) covalently coated with aminodextran and conjugated to monoclonal antibodies and protein. These results are:

| Ab T11:       | $K = 6.5 \times 10^5 M^{-1}$ | $n^s = 1.1 \times 10^{-7}$ mol/g |
|---|---|---|
| Ab KC16:      | $K = 3.2 \times 10^6 M^{-1}$ | $n^s = 6.9 \times 10^{-8}$ mol/g |
| Ab 1D3:       | $K = 3.2 \times 10^5 M^{-1}$ | $n^s = 1.7 \times 10^{-7}$ mol/g |
| Ab MO2:       | $K = 2.0 \times 10^6 M^{-1}$ | $n^s = 1.6 \times 10^{-7}$ mol/g |
| Ab KC48:      | $K = 2.5 \times 10^5 M^{-1}$ | $n^s = 7.6 \times 10^{-8}$ mol/g |
| Ab PLT-1:     | $K = 2.8 \times 10^5 M^{-1}$ | $n^s = 2.2 \times 10^{-7}$ mol/g |
| Streptavidin: | $K = 1.3 \times 10^6 M^{-1}$ | $n^s = 9.5 \times 10^{-8}$ mol/g |

In addition to ferrite core beads, the present invention was also evaluated using monoclonal antibodies conjugated to crosslinked gelatin-coated polystyrene beads. The binding constants for these antibodies, which compare favorably to both evaluations given above, are:

| Ab T8; | $K = 1.7 \times 10^6 M^{-1}$ | $n^s = 9.5 \times 10^{-8}$ mol/g |
|---|---|---|
| Ab T4; | $K = 2.5 \times 10^7 M^{-1}$ | $n^s = 3.5 \times 10^{-8}$ mol/g |

The results with the polystyrene beads indicate that the method of the present invention is not limited to magnetic spheres, but may be used with any colloidal particles that have a hydrophobic surface.

DESCRIPTION OF THE PREFERRED EMBODIMENT USING MAGNETIC BEADS

Preparation of Magnetite and Other Magnetic Particles in Gelatin Solution 10 mmol (5 mL) of 2M $KNO_3$ solution, 12.5 mmol (2.5 mL) of 5M KOH solution and 11.25 mL of double distilled water (DDW) were mixed and purged with $N_2$ gas for 10 minutes (Solution A). 6.25 mmol (6.25 mL) of 1M $FeSO_4$ solution and 25 mL of freshly prepared, $N_2$ purged, 2% type B, 225 Bloom, bovine skin gelatin solution [useful gelatin solution range is from about 0.8% to about 2.0%] were then added to Solution A in a Pyrex ® bottle, mixed, swept with $N_2$ gas, capped tightly, and placed undisturbed in an oven at 90° C. for 4 hours. After the suspension of black magnetite particles had reached room temperature, they were sonicated for ½ hour, washed with 1% type B, 225 Bloom gelatin solution, and then contacted with a large excess of 1% w/v gelatin as is the next step.

Metal ferrites may also be prepared using gelatin in situ in their preparation. In trials with other metals, namely $Mn^{2+}$, $Zn^{2+}$, $Co^{2+}$, $Ni^{2+}$, and, the molar ratio of $M^{2+}$:$Fe^{2+}$ was kept at 1:2, but nitrate was used instead of sulfate for $Co^{2+}$ and $Ni^{2+}$. The total metal-to-hydroxide molar ratio was maintained at 1:2; but the relative $KNO_3$ to total metal and $KNO_3$ to KOH molar ratios were altered. In preparing the mixed Mn/Zn ferrite, a 1:1 molar ratio of manganese sulfate to zinc sulfate and the same total molar amount of non-ferrous metal ions were used. The following is an example.

10 mmol (5 mL) of 2M $KNO_3$ solution, 18.75 mmol (3.75 mL) of 5M KOH solution and 6.875 mL DDW were mixed and purged with $N_2$ gas for 10 minutes (Solution C). 6.25 mmol (6.25 mL) 1M $DeSO_4$ solution, 3.125 mmol (3.125 mL) of 1M $Co(NO_3)$ solution and 25 mL of type B, 225 Bloom, bovine skin gelatin solution were mixed and purged with $N_2$ gas for 10 minutes. (Solution D). Solution D was added to Solution C in a Pyrex® bottle, mixed, swept with $N_2$ gas, capped tightly, and placed undisturbed in an oven at 90° C. for 5 hours. After the suspension of brown particles had reached room temperature, they were sonicated for $\frac{1}{2}$ hour, washed with 1% type B, 225 Bloom gelatin solution and then contacted with a large excess of 1% w/v gelatin as in th next step.

Using the methods described above, cobalt and nickel ferrite particles of about 0.1 and 0.2 $\mu$m in diameter and of spherical shape were formed in large, loosely-held brown aggregates. Zinc gave low yields of light brown magnetic material of less than 0.2 $\mu$m diameter even after 72 hours of heat treatment. Dark brown manganese ferrite particles of uniform, spherical shape and 0.3 $\mu$m diameter were obtained as single particles in 83-88% yields. Similar light brown manganese-zinc ferrite particles were produced in 49-55% yield after 72 hours of heat treatment at 90° C. For barium, the procedure was modified since $BaSO_4$ is insoluble in water. (Except for the case where barium is present, the divalent metals may be used as their chlorides or sulfates as well as their nitrates). Thus 6.25 mmol (6.25 mL) of 1M $FeCl_2$ solution, 0.5 mmol (5.0 mL) of 0.1 $Ba(NO_3)_2$ solution and 25 mL of 2% gelatin were mixed and purged with $N_2$ gas for 10 minutes (Solution D). Solution C and the remainder of the ferrite preparation procedure was unchanged except 10 mmol KOH solution (2 mL) was used and the heat treatment was continued for 20 hours. Black barium ferrite particles of uniform non-spherical shape with a 0.2 $\mu$m diameter were produced.

Preparation of Gelatin Coated Magnetic Particles

A quantity of magnetic particles, for example, manganese ferrite particles, of uniform size (0.3 $\mu$m) and spherical shape and prepared using in situ gelatin according to the procedures described above were contacted with a large excess of 1% w/v, type B, 225 Bloom aqueous gelatin solution. Alternately, preformed (i.e., formed by methods other than the in situ use of gelatin), dispersible magnetic particles, for example, manganese ferrite particles, of uniform size (0.3 $\mu$m) and spherical shape were contacted with a large excess of 1% w/v, type B, 225 Bloom gelatin solution at ambient temperature for approximately 60 minutes. The particles (either of the above) were then magnetically separated and washed five times with a 2% w/v, type A, 175 Bloom gelatin solution in 0.2M aqueous sodium chloride, pH 8.4. After washing, the particles were stored at ambient temperatures for up to several months as 2.5% w/v (weight/volume) solids suspension in a 2% w/v aqueous solution of the type A gelatin containing 0.2M sodium chloride, 0.1% w/v sodium azide at pH 8.4. Provided the azide content of the storage solution is maintained, the suspension can be stored for up to about 3 months. The magnetic particles so formed have two gelatin layers, a first layer of type B gelatin and a second layer of type A gelatin.

Crosslinking the Adsorbed Gelatin 62.5 L of 25% aqueous glutaraldehyde (0.156 mmol) solution was added to 120 ml of 1% aqueous polyvinylpyrrolidone (MW=40,000) in 0.2M aqueous sodium chloride, pH 7.2. To this, 5 ml of the 2.5% solid suspension prepared above was added to the glutaraldehyde solution and the resulting suspension was mixed at ambient temperature for a time in the range of 3-15 minutes, preferably about 6 minutes.

Blocking of Unreacted Aldehyde Groups 0.105 ml of 99% ethylenediamine (1.56 mmol) was added to a 125 ml suspension of the fixed, gelatin coated magnetic particles (0.1% w/v solids) in 1% PVP solution, 0.2M in sodium chloride, pH 7.2. The resulting suspension was mixed for a time in the range of about 1 to 4 hours, preferably about 2 hours, in a 250 ml tissue culture flask. At the end of the mixing time, 1.25 ml of a 10 mg/ml solution of sodium borohydride ($NaBH_4$) in 0.1 mM KOH was added to the magnetic particles and the resulting suspension was mixed for an additional 15 minutes. The particles were then magnetically separated and washed a plurality, preferably three, times with 0.2M aqueous sodium chloride.

Reaction with Fixed Gelatin's Carboxylate Residues 2.11 ml of 99% ethylenediamine were added to an 118 ml suspension of the aldehyde-blocked beads, 0.1% w/v solids, in 0.2M aqueous NaCl. The resulting suspension was physically and sonically mixed for approximately 15 minutes. After this mixing, 4.5 ml of 10 mg/ml EDAC in 0.2M NaCl was added and the suspension was first physically and sonically mixed for approximately 15 minutes, and finally physically mixed for a time in the range of about 8-16 hours. The contents of the flask were then magnetically separated, washed a plurality of times with 1×PBS, sonically mixed in 1×PBS or approximately 30 minutes, and finally concentrated to 5 ml of 2.5% w/v solids in 1×PBS. For large scale (100×) preparations, the previous aldehyde blocking step and the EDAC coupling step have been combined to avoid multiple separations and washings. The combination of steps did not result in any loss of activity in the final antibody-conjugated beads.

Activation of Diamine Treated Particles with Sulfo-SMCC

In general, 27 $\mu$L of freshly prepared 10 mg/ml sulfo-SMCC in 1×PBS was used per milliliter of 2.5% w/v magnetic particle suspension. In a typical preparation, 135 $\mu$L of the sulfo-SMCC solution was added to 5 ml of 2.5% w/v particles. The mixture was then roller mixed in a 15 ml plastic centrifuge tube for approximately one hour, sonically mixed for approximately 5 minutes, magnetically separated, and washed a plurality of times with 1×PBS.

The functionalized, crosslinked, gelatin coated particles resulting from the above series of steps have pendent maleimidyl groups and are suitable for a variety of medical and/or biological uses. If the substance which is desired to be conjugated to the particles has a sufficiency of active sulfhydryl groups, activation of that substance is not necessary, and the following step may be skipped.

Antibody Activation with 2-iminothiolane Hydrochloride

A 51.24 mg/ml concentrate of T11 monoclonal antibody in 1×PBS containing 0.1% NaN₃ was prepared. For 10 mg of T11 antibody and 15 mg/ml antibody concentration during coupling, the total reaction volume should be 0.667 ml. Using a 15:1::IT:T11 activation ratio, 0.9375 $\mu$mol (0.129 mg) IT (65 $\mu$L of 2 mg/ml IT) in 1×PBS is required. Therefore, 0.407ml of 1×PBS solution was added to 0.195 ml of T11 concentrate, to which resulting solution an additional 65 $\mu$L of 2 mg/ml IT solution was added. The net resulting solution was roller mixed in a tube reactor for 1 hour. The content of the reaction tube was then applied to the top of a 20 ml G-50 Sephadex column, equilibrated and washed with 100 ml 1× x PBS. The derivatized antibody was eluted using 1×PBS and a plurality of 2.5 ml fractions were collected with the aid of a UV monitor. Fractions in the middle of the band absorbing at 280 nm were pooled and the $A_{280}$ value was used to determine T11/IT antibody concentration. Typically, the T11/IT concentration was about 3.0 mg/ml. The T11/IT solution may be concentrated by solvent removal.

Conjugation of T11/IT with Sulfo-SMCC Derivatized Particles

In a laboratory scale conjugation, total volume 5 ml, the concentration of particles was 2.5% w/v solids and the T11/IT concentration was 0.9 mg/ml. In one sample, when the purified T11/IT solution concentration was 1.850 mg/ml, then 2.392 ml of T11/IT antibody solution in 1×PBS was added to 5 ml of 2.5% w/v solids sulfo-SMCC activated particles which had been preconcentrated by the removal of 2.432 ml of supernatant. The T11/IT solution was added to the particles in 0.5 ml increments with sonic and rapid physical mixing between additions. The resultant solution was then roller mixed in a 15 ml tube for approximately two hours. A 1 ml test sample was then taken, filtered through a low-protein binding 0.2 $\mu$m filter, and the filtrate analyzed spectrophotometrically for T11 antibody by measuring the absorbance at 280 nm; $A_{280}$=c (supernatant) =0.3986 mg/ml. [measurement by difference, c (surface)=c (total)−c (supernatant)]. Thus c (surface)=0.9 mg/ml−0.3986 mg/ml=0.501 mg/ml. This translates to a T11 surface loading of 20 mg T11 per gram particles or, for a specific surface area of 4.89 m²/g for manganese ferrite particles, a 4.1 mg T11/m² particle surface area. Similar procedures with 2- and 3-fold dilutions of particle concentration, but the same total antibody concentration during conjugation, gave higher surface antibody loading. However, a limitation was reached when a 4-fold dilution of the particles concentration did not yield higher surface coverage of antibody.

Blocking Unreacted Maleimidyl and Sulfhydryl Groups

Unreacted maleimidyl groups on the sulfo-SMCC activated particles were blocked with L-cysteine after antibody conjugation. Typically, 0.480 ml of 5 mg/ml L-cysteine in 1×PBS was added to remaining 4 ml of the conjugation mixture of the previous step and the resulting solution was roller mixed for 15 minutes. Unreacted sulfhydryl groups were blocked by the addition of 0.534 ml of 20 mg/ml iodoacetamide in 1×PBS followed by the addition of 0.100 ml of 1M, pH 9.8 sodium borate buffer solution. The resulting solution was roller mixed for 30 minutes, the blocked conjugation mixture was magnetically separated and the particles washed three times with 1×PBS containing 1% bovine serum albumin (fraction V, heat shock) and 0.1% NaN₃ (BSA buffer solution). After washing, 4 ml of the foregoing BSA solution was added to the particles, the particles roller mixed for approximately 1 hour, stored at 4° C. for a time in the range of about 8–16 hours, magnetically separated and washed three additional times with BSA buffer.

Antibody containing particles prepared according to the method described herein have been found useful in various cell separation assays. The biological substances used in assays utilizing the invention may be selected from the groups consisting of normal or non-normal T-cells, B-cells, leukocytes, viruses, erythrocytes, cells of the breast, uterus, colon, kidney, liver, lung, testes, stomach, thyroid and parathyroid, and the like; provided that the biological substance contains an antigenic determinant capable of binding to an antibody.

In an embodiment of the invention equivalent to the magnetic particle embodiment described above, the maleimidyl groups and the sulfhydryl groups are transposed. That is, the crosslinked gelatin coated particles are derivatized to have pendent groups ending in reactive sulfhydryl groups in place of the maleimidyl groups described above and the antibodies are derivatized to have reactive maleimidyl groups in place of the sulfhydryl groups described above. The methods used to prepare this equivalent embodiment are the same as described above. In both cases, the antibody is connected to the gelatin surface by a molecular bridge prepared as described.

The following examples are given to illustrate the utility of the claimed invention and are not to be taken as limiting said invention.

EXAMPLE 1

Protocol for Magnetic Bead Depletion of T-cell and B-cell Populations.

Mononuclear cells (MNC) were obtained from whole blood samples by density isolation on Ficoll-hypaque gradients and washed in PBS. 1×10⁶ MNC in 1 ml PBS were added to a series of tubes containing 5, 10, 25, 50 and 100 $\mu$L of the monoclonal antibody (MoAb) conjugated magnetic particle suspension (2.5% w/v) being tested. Two tubes were set up for each depletion and for the undepleted control. The resulting suspensions were then nutated for 3 minutes in a multi-tube vortexer or a single tube nutator. At the end of incubation, the cell suspension was placed for a total of 2 minutes in the magnetic field provided by a single tube magnetic rack. At the end of the magnetic separation, unbound cells were extracted by withdrawing all the clear liquid from the center of the tube with a Pasteur pipet.

For T- or B-cells (T11, T3, T4, T8, B1, B4), the cell suspension collected after depletion was compared directly to the original cell suspension prior to particle depletion. The samples, original and depleted, were centrifuged for 5 minutes at 1200 rpm and the supernatant decanted to leave approximately 100 μL of PBS remaining in each tube. One tube of each pair of depletion tubes was then stained with 10 μL CYTO-STAT® MsIgG1-RD1/MsIgG1-FITC control reagent (MS) and the other tube was stained with 10 μL CYTO-STAT®T11-RD1/B4-FITC reagent (for T11, T3, B1 or B4 depletions) or with 10 μL of T4-RD1/T8-FITC reagent (for T4 or T8 depletions) at room temperature for 10 minutes. At the end of incubation, 500 μL of PBS were added to each sample and the samples were analyzed by flow cytometry. The samples were analyzed on the EPICS® Profile using the MBead 2-Color program. (EPICS and CYTO-STAT® are registered trademarks of Coulter Corporation). As the original sample stained with MS control reagent was being run, it was checked to determine whether the lymphocyte population was fully incorporated in Bitmap 1, and adjustments were made if necessary. The left side of discriminator 2 was set for each fluorescence histogram on the channel which would give <1% positive staining. This was done for each sample stained with MS control reagent and then the corresponding tube stained with specific antibody was analyzed. The data were collected and recorded as the absolute number of positive staining cells in the red and green histograms (T and B or T4 and T8) not percent positive. Test results are summarized below.

EXAMPLE 2

Protocol for Magnetic Bead Depletion of Red Blood Cells (RBC).

100 μL of Na4EDTA-anticoagulated whole blood was placed in a series of reaction tubes. To each tube, 25 to 150 μL of KC-16 conjugated magnetic particles suspension (2.5% w/v) was added and the total volume was adjusted to 250 μL using PBS. The suspensions were nutated for 3-5 minutes in a multitube vortexer or a single tube nutator at low mixing speed. When nutation was completed, 1 ml of PBS was added to each sample tube which was then placed on a magnetic rack for 2-5 minutes. All the supernatant was removed from each tube using a Pasteur pipet and saved in labelled tubes. Samples were analyzed on a Coulter S-plus IV or similar rbc counter as total rbc number/ml whole blood. The positive control was 100 μL whole blood plus 1.150 ml PBS to give 100% rbc count and the negative control was 100 μL whole blood plus 1.150 ml of Batch lyse or similar lysing agent to give 0% rbc count. Percentage of rbc depleted=100%- [(rbo count in sample tube)/(100% rbc count)].

EXAMPLE 3

Protocol for Magnetic Bead Depletion of Leukocytes 100 ml of Na4EDTA-anticoagulated whole blood were collected, divided among a number of centrifuge tubes and centrifuged at 500 g for 10 minutes. The majority of plasma was removed and the buff colored layer of cells from each tube was removed, pooled together and centrifuged at 500 g for an additional 10 minutes. The buff colored cells and the plasma constitute the leuko-rich whole blood which should have an rbc count no greater than $8.0 \times 10^9$/ml and a white blood cell (wbc) count of $2-4 \times 10^7$/ml.

100 μL of leuko-rich whole blood was pipetted into a number of reaction tubes. An amount of 10 to 160 μL of magnetic bead suspension (2.5% w/v) was then pipetted into each tube followed by the addition of 200 μL of 1×PBS. (N.B. Lower titer points with 10 to 40 μL of beads should be run first. Additional beads were added only if endpoint depletion was not obtained at 40 μL). Each tube was nutated for 3-5 minutes at low speed. 2 ml of 1×PBS was then added, the contents of a tube mixed and then magnetically separated for 2 minutes. All supernatant liquid was removed and placed in a duplicate tube which was then centrifuged at 400 g for 5 minutes. The resulting supernatant was then carefully removed by pipette and analyzed.

The leuko-rich or the leuko-depleted whole blood samples were analyzed by the addition of 10 μL of single or dual color antibody preparation designed to discriminate for the depletion of specific cells from a mixture of cells. For example, when T11-conjugated magnetic beads were used in depletion, T11-B4 dual color was used to discriminate between actual T11+ cell depletion and the non-specific depletion of T11- cells (i.e. B-cells). The mixture was vortexed and incubated for 10 minutes at room temperature in the dark. Controls were isotype control and antibody control with undepleted cells. The tubes were then placed on a Coulter EPICS® Q-prep, or similar instrument, and run on the 35 second lyse mode. After the rbc were lysed and the samples fixed (Q-prep), all samples were analysed on a Coulter EPICS® Profile flow cytometer or similar instrument. This procedure is required to obtain data as actual number of cells per volume of sample. Programs available on Profile were used to analyze lymphocytes and monocyte-myeloid populations.

Summary of Test Results using the Protocols of Examples 1-3

1. In a T11/B4 lymphoid cell assay, the undepleted control gave 97,209 T11+, 18,240 B4+, 19,717 monocyte and 25,381 granulocyte counts. After depletion with 10 μL of 2.5% w/v solids magnetic beads conjugated with T11 antibody, the counts were 15,826, 20,181, 19,954 and 30,972 respectively. Depletion with 20 μL T11 antibody conjugated beads gave 2,256, 20,989, 20,874 and 31,965 counts; 30 μL gave 1,150, 21,428, 20,697 and 35,362 counts; and 40 μL gave 644, 21,232, 19,817 and 33,935 counts, all respectively.

2. In a T4/T8 lymphoid cell assay, the undepleted control, which contained $4.1 \times 10^5$ T8 and $7.9 \times 10^5$ T4 cells, gave 54,415 T4 and 27,906 T8 counts. After depletion with 10, 20 and 30 μL of 2.5% w/v solids magnetic beads conjugated with T8 antibody the counts were 57,030 and 12, 59,538 and 6, and 60,905 and 5, respectively.

3. In an erythrocyte/thrombocyte assay, the undepleted control contained $4.5 \times 10^6$ wbc, $4.4 \times 10^8$ rbc and $4.7 \times 10^7$ platelets. Depletion experiments were conducted using 20, 40, 60 and 80 μL of 2.5% w/v solids magnetic beads conjugated with KC-16 antibody. The wbc, rbc and platelets remaining after depletion were 20 μL:$4.4 \times 10^6$ wbc, $1.6 \times 10^8$ rbc and $4.3 \times 10^7$ platelets; 40 μL:$4.6 \times 10^6$ wbc, $1 \times 10^7$ rbc and $4.5 \times 10^7$ platelets; 60 μL:$4.5 \times 10^6$ wbc, $1 \times 10^7$ rbc and $4.3 \times 10^7$ platelets; and 80 μL:$4.5 \times 10^6$ wbc, $1 \times 10^7$ rbc and $4.3 \times 10^7$ platelets. The results indicate that 40 μL of 2.5% solids beads which contained $1.85 \times 10^{10}$ particles removed $4.3 \times 10^8$ rbc, thus giving a particle-to-rbc ratio of 43.

4. In a myeloid cell assay, the undepleted control gave 73,821 lymphocyte, 13,426 monocyte and 55,661 granulocyte counts. Depletion studies were conducted using 10, 20, 30 and 40 μL of 2.5% w/v solids magnetic beads conjugated with KC-48 antibody. The results were 10 μL:70,330, 9,309 and 340 counts; 20 μL:68,414, 2,006 and 1,332 counts; 30 μL:62,966, 1,597, and 922 counts; and 40 μL:59,340, 1,546 and 899 counts, all respectively.

A similar depletion study was conducted using 10, 20, 30 and 40 μl of 2.5% w/v solids magnetic beads conjugated with 1D3 antibody. The results were 10 μL:13,839 and 1,597 counts; 20 μL:73,198, 8,653 and 1,216 counts; 30 μL:65,667, 2,590 and 2,130; and 40 μL:66,276, 1,906 and 1,686 counts, all respectively.

A further depletion study was conducted using 10, 20, 30 and 40 μL of 2.5% w/v solids magnetic beads conjugated with MO2 antibody. The results were 10 μL:72,563, 3,107 and 56,520 counts; 20 μL:72,905, 3,616 and 34,533 counts; 30 μL:69,644, 1,618 and 32,313 counts; and 40μL:69,477, 1,210 and 30,899 counts, all respectively.

5. In an erythrocyte/thrombocyte assay, the undepleted control contained $7\times10^6$ wbc, $4.9\times10^{10}$ rbc and $3.0\times10^7$ platelets. Depletion studies were conducted using 20, 40, 60 and 80 μL of 2.5% w/v solids magnetic beads conjugated with PLT-1 antibody. The results, after depletion, were 20 μL: $10\times10^6$ wbc $5.4\times10^{10}$ rbc and $1\times10^6$ platelets; 40 μL:$10\times10^6$ wbc, $5.8\times10^{10}$ rbc and $1\times10^6$ platelets; 60 μL:$7\times10$ 6 wbc, $5.1\times10^{10}$ rbc and $1\times10^6$ platelets; and 80 μL:$10\times10^6$ wbc, $5.6\times10^{10}$ rbc and 0 platelets.

DESCRIPTION OF THE PREFERRED EMBODIMENT USING POLYSTYRENE LATEX PARTICLES

Preparation of Gelatin Coated Polystyrene Latex Particles

Sulfate polystyrene latex particles (IDC Corporation, Portand, Oregon) of uniform size (2.17 μL±3.0%) and spherical shape were dispersed in distilled water and centrifuged for 10 minutes at 3000 rpm. The supernatant liquid was discarded and the particles were resuspended in 1% aqueous, type A, 175 Bloom gelatin at 2.5% w/v solids, sonically mixed for 1 minute to aid redispersion and roller mixed for 8-16 hours.

Crosslinking the Adsorbed Gelatin and Blocking Unreacted Aldehyde Groups

A 0.300 μL aliquot of 25% aqueous glutaraldehyde (0.749 mmol) was added to 575 ml phosphate buffered saline (1×PBS) containing 1% polyvinylpyrrolidone (40,000 MW). 25 ml of 2.5% w/v solids sulfate polystyrene latex particles in 1% gelatin solution were then added to the glutaraldehyde solution. The resulting suspension was placed in a 1L polypropylene centrifuge bottle and roller mixed for 6 minutes. After mixing, 0.505 ml of 99% ethylenediamine (7.49 mmol) was added to the 600 ml of particles in 1×PBS and the resulting suspension was roller mixed for about 2-3 hours. 6.0 ml of 10 mg/ml NaBH4 in 0.1 mM aqueous KOH were added and the suspension again roller mixed for 15 minutes. The particles were washed three times with 0.2M aqueous NaCl by centrifugation and decantation. After washing, the particles were resuspended in 0.2M NaCl to yield 24 ml of 2.5% w/v solids suspension.

Coupling of Ethylenediamine to the Carboxylate Residues of Gelatin Coated on Polystyrene Latex Particles A 0.404 ml aliquot of 99% ethylenediamine (6.00 mmol) was mixed with 24 ml of fixed, aldehyde blocked polystyrene particles, 2.5% w/v solids. A 0.960 ml sample of 10 mg/ml EDAC (0.050 mmol) in 0.2M NaCl solution was added to the particles and roller mixed for 8-16 hours in a 50 ml centrifuge tube. The contents of the tube were washed five times with 1×PBS by centrifugation for 10 minutes at 3000 rpm and decantation. The particles were then resuspended in sufficient 1×PBS to give a total volume of 24 ml.

Activation by Sulfo-SMCC and Antibody Coupling to the Gelatin Coated Polystrene Latex Particles The coupling of monoclonal antibodies to gelatin coated polystyrene particles was carried out using the same procedures as followed for magnetic beads, except that separation of the particles was accomplished by centrifugation for 10 minutes at 3000 rpm followed by decantation of the supernatant liquid.

EXAMPLE 4

T4 and T8 Cell Population Assays Using Monoclonal Antibody Covalently Bound to Gelatin Coated Polystyrene Latex Particles 15 μL of KC-48-conjugated magnetic bead suspension (2.5% w/v) were added to 50 μL of whole blood. The mixture was gently vortexed for 15 seconds and magnetically separated. 28 μL of the supernatant were transferred to a new test tube and 15 μL of T4- or T8-conjugated, gelatin coated polystyrene latex beads (2.5% w/v) were added to the tube. The contents of the tube were then vortexed for 15 seconds. 300 μL of Batch lyse for red blood cells were added, the mixture vortexed for 4 seconds, 120 μL of a lyse quencher added and the mixture again vortexed for 4 seconds. The resulting sample was analyzed on a Coulter VCS or similar instrument for the population of shifted T-cells. Controls were whole blood and whole blood with granulocytes removed by KC-48-conjugated magnetic beads. The percent of T4 or T8 cells in a sample equals the cell population shifted into the KC-48 depleted region of DC versus opacity, (RF-85)/DC, plot/[(cell population shifted into KC-48 depleted region)+(cell population in lymphocyte region)]×100.

In an embodiment of the invention equivalent to the latex particle embodiment described above, the maleimidyl groups and the sulfhydryl groups are transposed. That is, the crosslinked gelatin coated particles are derivatized to have pendent groups ending in reactive sulfhydryl groups in place of the maleimidyl groups described above and the antibodies are derivatized to have reactive maleimidyl groups in place of the sulfhydryl groups described above. The methods used to prepare this equivalent embodiment are the same as described above.

We claim:

1. Colloidal particles in which each particle comprises a solid core coated with two layers of water soluble gelatin having a plurality of pendant functional groups, said gelatin layers comprising a first layer of type B, alkali cured gelatin of Bloom in the range 60 to 225 and a second layer of type A, acid cured gelatin of Bloom in the range 60 to 300, and said layers on the individual particles being crosslinked by the action of a chemical crosslinking agent such that aid particles can be stored as predominantly discrete colloidal particles.

2. Particles in accordance with claim 1 wherein said solid core consists of a magnetic particle having a hydrophobic surface.

3. Particles in accordance with claim 1 wherein said solid core is in the size range of approximately 0.1 to 5.0 microns.

4. Particles in accordance with claim 1 wherein said solid core is in the size range of approximately 0.1 to 1.0 microns.

5. Particles in accordance with claim 1 wherein said chemical crosslinking agent is glutaraldehyde.

6. Particles in accordance with claim 1 wherein said functional groups are amino groups.

7. Particles in accordance with claim 1 wherein said functional groups are selected from the group consisting of maleimidyl or sulfhydryl groups.

8. Particles in accordance with claim 7 wherein a biological substance is bonded to either of said maleimidyl or sulfhydryl groups.

9. Particles in accordance with claim 8 wherein said biological substance is selected from the group consisting of polyclonal antibodies or monoclonal antibodies.

10. Particles in accordance with claim 8 wherein said biological substance has reactive substituents selected from the group consisting of sulfhydryl substituents and maleimidyl substituents, and further provided that when the particle functional group is maleimidyl, the biological substance substituent is sulfhydryl and when the particle functional group is sulfhydryl, the biological substance substituent is maleimidyl.

11. Particles in accordance with claim 9 wherein said antibodies have reactive sulfhydryl or maleimidyl substituents.

12. Particles in accordance with claim 1 wherein said functional groups comprise biological substances bonded to said gelatin.

13. Particles in accordance with claim 12 wherein said biological substances are selected from the group consisting of polyclonal antibodies and monoclonal antibodies.

14. Particles in accordance with claim 1 wherein said functional groups are polyclonal antibodies.

15. Particles in accordance with claim 1 wherein said functional groups are monoclonal antibodies.

16. A process for the preparation of discrete colloidal particles each having a solid core coated with biodegradable, crosslinked gelatin having pendent functional groups, said process comprising:
(a) adsorbing as a first layer, a type B, alkali cured gelatin of Bloom in the range 60 to 225 and as a second layer, a type A, acid cured gelatin of Bloom in the range 60 to 300 onto the surface of the solid core particles;
(b) crosslinking the coated gelatin by reaction with a chemical crosslinking agent;
(c) blocking free, unreacted crosslinking agent functional groups present on the surface of the product of step (b) by reaction of said groups with a sufficiency of a diamine or a polyamine such that one of the amine —NH$_2$ groups reacts with said unreacted crosslinking agent functional group and the other NH$_2$ group or groups remain unreacted;
(d) separating the blocked, crosslinked gelatin coated particles of step (c) and washing the same;
(e) coupling residual gelatin carboxylate groups inherently present on said particles of steps (c) and (d) by reaction with a diamine or a polyamine such that one of the amine NH$_2$ groups reacts with a carboxylate group and the other NH$_2$ group or groups remain unreacted; and
(f) further derivatizing the particles of step (e) by reaction with a bifunctional bridging group to obtain said colloidal particles having pendent functional groups.

17. The process according to claim 16 wherein said solid core particles consist of magnetic particles having a hydrophobic surface.

18. The process in accordance with claim 16 wherein said core particles are in the size range of approximately 0.1 to 5.0 microns.

19. The process in accordance with claim 16 wherein said core particles are in the size range of approximately 0.1 to 1.0 microns.

20. The process in accordance with claim 17 wherein the Bloom Number is approximately 175.

21. The process in accordance with claim 16 wherein said chemical crosslinking agent is glutaraldehyde.

22. The process in accordance with claim 16 wherein said diamine is selected from the group consisting of ethylenediamine, 1,3-diaminopropane, 1,4-cyclohexanediamine, 1,4-cyclohexenediamine, 1,4-phenylenediamine, and diethylene triamine.

23. The process in accordance with claim 16 wherein the preferred diamine is ethylenediamine.

24. The process in accordance with claim 16 wherein said functional groups are selected from the group consisting of maleimidyl groups and sulfhydryl groups.

25. The process in accordance with claim 16 wherein said functional groups are biological substances attached to the product of step (e) or (f) and selected from the group consisting of biological substances having or derivatized to have reactive sulfhydryl or maleimidyl substituents.

26. The process in accordance with claim 25 wherein said biological substances are selected from the group consisting of polyclonal antibodies and monoclonal antibodies.

27. Particles having an antibody covalently bonded thereto comprising:
(a) a colloidal sized solid core material;
(b) a gelatin coating adsorbed onto the surface of said solid core and crosslinked thereon by a chemical crosslinking agent, said gelatin coating comprising first layer of type B, alkali cured gelatin of Bloom in the range 60 to 225 and a second layer of type A, acid cured gelatin of Bloom in the range of 60 to 300;
(c) an antibody; and
(d) a bridging group having an end covalently bonded to said crosslinked gelatin surface and another end covalently bonded to said antibody.

28. Particles in accordance with claim 27 wherein said solid core material is in the size range of approximately 0.1 to 5.0 microns.

29. Particles in accordance with claim 28 wherein said solid core material is in the size range of 0.1 to 1.0 micron.

30. Particles in accordance with claim 27 wherein said solid core material consists of magnetic particles having a hydrophobic surface.

31. Particles in accordance with claim 27 wherein said crosslinking agent is glutaraldehyde.

32. Particles in accordance with claim 27 wherein said bridging group contains a polyamine having an amine group bonded to said crosslinked gelatin surface and another amine group or groups bonded to a moiety having a reactive maleimidyl or sulfhydryl group, said polyamine being selected from the group consisting of ethylenediamine, 1,3-diaminopropane, 1,4-cyclohexanediamine, 1,4-cyclohexenediamine, 1,4-phenylenediamine, and diethylenetriamine.

33. The particles in accordance with claim 32 wherein the polyamine is ethylenediamine.

34. Particles in accordance with claim 27 wherein said antibody is selected from the group consisting of polyclonal antibodies and monoclonal antibodies.

35. The particles of claim 27 wherein the antibody is a monoclonal antibody.

36. The particles of claim 27 wherein said antibody has a reactive substituents selected from the group consisting of a sulfhydryl substituent and a maleimidyl substituent, said sulfhydryl substituent being naturally present on said antibody or being generated by modification of an amino group or groups naturally present on said antibody with 2-iminothiolane hydrochloride, and said maleimidyl substituent be present by modification of an amino group or groups on said antibody with a maleimidyl containing reagent.

37. A process for preparing particle bound antibodies comprising:

(I)
(a) coating a solid core material with gelatin by mixing said core material with a 1% w/v aqueous gelatin solution of type B, alkali cured gelatin of Bloom in the range 60 to 225, and isolating and washing said particles with a solution of said type B gelatin;

(b) separating the particles of step (a) and washing the particles with an approximately 2% aqueous solution of Type A, isoelectric point pH 8.3–8.5, 175 Bloom gelatin;

(c) maintaining the washed particles of step (b) in suspension in a 2% aqueous solution of type A, isoelectric point pH 8.3–8.5, gelatin until used in step (d), a time in the range of about 8 hours to three months;

(d) adding the suspension of step (c) to a solution of glutaraldehyde in about 1% polyvinylpyrrolidone 0.2M sodium chloride solution at about pH 7.2 and mixing the resulting suspension at ambient temperature for a time in the range of 3 to 15 minutes, thereby crosslinking the gelatin adsorbed on the core's surface;

(e) adding ethylenediamine to the suspension of step (d) and mixing the new suspension for a time in the range of 1 to 4 hours;

(f) adding $NaBH_4$ to the suspension step of (e) and mixing the new suspension;

(g) separating the particles of step (f) from the suspending solution and washing the particles with 0.2M aqueous NaCl;

(h) reacting, with mixing, the resultant particles of step (f) or (g) with ethylenediamine in 0.2M NaCl aqueous solution containing 1-ethyl-3-(3-dimethylaminopropyl)-carbodiimide at ambient temperature;

(i) separating the particles of step (h) from the reaction solution and washing them with phosphate buffered saline solution;

(j) reacting the particles of step (i) with a bifunctional bridging reagent in phosphate buffered saline solution at ambient temperature for a time in the range of approximately 0.50 to 1.5 hours to prepare particles having reactive terminal maleimidyl or sulfhydryl groups bound to the particles' surface; and (k) separating the particles of step (j) and washing them with phosphate buffered saline solution;

(II) separately preparing an antibody for conjugation to the particles of step (I)(k) by generating reactive substituents consisting of sulfhydryl groups or maleimidyl groups on said antibody;

(III) reacting the particles of step (I)(k) and the antibody of step (II), with mixing, for a time in the range of about 1–3 hours, whereby said reactive substituents of said antibody are coupled to the particles' reactive groups, separating the resulting antibody containing particles from the reaction medium and washing them with buffered saline solution;

(IV) blocking unreacted groups present on the product of step (III); and (V) separating and washing the antibody containing particles of step (IV) with about 1% bovine serum albumin in 0.1% $NaN_3$ in phosphate buffered saline solution, storing the washed particles in said solution at about 4° C. for a period in the range of 8 to 16 hours, separating the antibody containing particles, again washing the particles with bovine serum albumin buffer solution, and storing the resulting antibody containing particles in about 1% bovine serum albumin, 0.1% $NaN_3$ in phosphate buffered saline solution until required for use.

38. The process in accordance with claim 37 wherein said solid core material consists of a magnetic particle having a hydrophobic surface.

39. The process in accordance with claim 37 wherein said particles have a size of approximately 0.1 to 5.0 microns.

40. The process in accordance with claim 37 wherein said particles have a size of approximately 0.1 to 1.0 micron.

41. The process in accordance with claim 37 wherein said antibody is selected from the group consisting of polyclonal antibodies and monoclonal antibodies.

42. The process in accordance with claim 37 where said antibody is a monoclonal antibody.

43. A process for the separation and analysis of a biological substance comprising:

(a) contacting a solution containing a biological substance with an antibody covalently bound to the surface of a crosslinked gelatin coated solid core particle wherein said gelatin coating comprises a first layer of type B, alkali cured gelatin of Bloom in the range 60–225 and a second layer of type A, acid cured gelatin of Bloom in the range of 60–300;

(b) incubating the mixture of step (a) for a time and at a temperature sufficient to insure the formation of a complex between said biological substance and said antibody;

(c) biological substance containing solution;

(d) washing the separated particles; and (e) analyzing the separated particles of step (d) for the presence of said complex and/or the solution of step (c) for the presence and/or the absence of an uncomplexed biological substance.

44. The process according to claim 43 wherein said antibody is selected from the group consisting of polyclonal antibodies or monoclonal antibodies.

45. The process according to claim 43 wherein said biological substance is selected from the group consisting of T-cells, B-cells, leukocytes, viruses, erythrocytes, cells of the breast, uterus, colon, kidney, liver, lung, testes, stomach, thyroid and parathyroid, provided that said substance ;contains an antigenic determinant capable of binding to an antibody.

46. The process according to claim 43 wherein said antibody containing particle comprises
    (a) a solid core of colloidal size;
    (b) a gelatin coating as specified in claim 43 adsorbed on the surface of said core and crosslinked thereon by a chemical crosslinking agent;
    (c) a functional group covalently attached to said crosslinked gelatin surface of step (b); and
    (d) an antibody covalently bound to said functional group.

47. The process in accordance with claim 43 wherein the core of said solid core particle consists of a magnetic core having a hydrophobic surface.

48. The process in accordance with claim 43 wherein the core of said solid core particle has a size in the range of approximately 0.1 to 1.0 micron.

* * * * *

UNITED STATES PATENT AND TRADEMARK OFFICE
CERTIFICATE OF CORRECTION

PATENT NO. : 5,169,754

DATED : December 8, 1992

INVENTOR(S) : Olavi Siiman, Alexander Burshteyn, Ravinder K. Gupta

It is certified that error appears in the above-identified patent and that said Letters Patent is hereby corrected as shown below:

Column 8, line 11, change "carboxyate" to --carboxylate--;

Column 9, line 68, change "$1/n_2^2$" to --$1/n_2^s$--;

Column 10, line 7, after "equation" change "$1/n_2$" to --$1/n_2^s$--;

line 8, change "ns" to --$n^s$--;

Column 11, line 3, after "and" insert --$(M^{2+})$--;

line 15, change "$DeSO_4$" to --$FeSO_4$--;

line 26, change "th" to --the--;

Column 12, line 47, after "PBS" change "or" to --for--;

Column 13, line 23, change "1 X x PBS" to --1X PBS--

Column 15, line 49, after "[(" change "rbo" to --rbc--;

Column 17, line 9, change "$\mu$L: 13,839" to --$\mu$L: 76,405, 13,839--;

Column 19, line 2, change "aid" to --said--;

UNITED STATES PATENT AND TRADEMARK OFFICE
CERTIFICATE OF CORRECTION

PATENT NO. : 5,169,754

DATED : December 8, 1992

INVENTOR(S) : Olavi Siiman, Alexander Burshteyn, Ravinder K. Gupta

It is certified that error appears in the above-identified patent and that said Letters Patent is hereby corrected as shown below:

Column 20, line 50, change "first layer" to

--a first layer--;

line 61, change "claim 28" to --claim 27--;

Column 22, line 63, before "biological" insert

--separating the solid particles of step (b)

from the--;

Column 23, line 9, after "substance" delete --;--.

Signed and Sealed this

Eighth Day of February, 1994

Attest:

BRUCE LEHMAN

Attesting Officer

Commissioner of Patents and Trademarks